United States Patent [19]

Chen et al.

[11] Patent Number: 4,468,335

[45] Date of Patent: Aug. 28, 1984

[54] BRANCHED ALKYLPOLYETHOXYPROPANE SULFONATES AND THEIR USE IN ENHANCED OIL RECOVERY

[75] Inventors: Catherine S. H. Chen, Berkeley Heights; Albert L. Williams, Princeton, both of N.J.

[73] Assignee: Mobil Oil Corporation, New York, N.Y.

[21] Appl. No.: 373,550

[22] Filed: Apr. 30, 1982

Related U.S. Application Data

[63] Continuation-in-part of Ser. No. 259,215, Apr. 30, 1981, , and Ser. No. 259,216, Apr. 30, 1981.

[51] Int. Cl.[3] .............................................. E21B 43/22

[52] U.S. Cl. .............................. 252/8.55 D; 166/274; 166/275; 252/8.55 R; 260/513 R

[58] Field of Search ..................... 252/8.55 R, 8.55 D; 166/274, 275; 260/513 R

[56] References Cited

U.S. PATENT DOCUMENTS

| | | | |
|---|---|---|---|
| 3,856,738 | 12/1974 | Bodesheim et al. | 260/513 R |
| 4,018,278 | 4/1977 | Shupe | 252/8.55 X |
| 4,077,471 | 3/1978 | Shupe | 252/8.55 X |
| 4,133,385 | 1/1979 | Kalfoglou | 252/8.55 X |
| 4,157,115 | 6/1979 | Kalfoglou | 166/274 |
| 4,181,178 | 1/1980 | Savins | 252/8.55 X |
| 4,187,073 | 2/1980 | Schievelbein | 252/8.55 |
| 4,214,999 | 6/1980 | Carlin et al. | 252/8.55 D |
| 4,222,957 | 9/1980 | Watts, Jr. et al. | 260/513 R |
| 4,231,427 | 11/1980 | Kalfoglou | 252/8.55 X |
| 4,307,782 | 12/1981 | Schievelbein | 252/8.55 D |
| 4,318,816 | 3/1982 | Schievelbein | 252/8.55 D |
| 4,319,636 | 3/1982 | Kudchadker et al. | 252/8.55 D |
| 4,330,418 | 5/1982 | Glinsmann et al. | 252/8.55 D |
| 4,340,492 | 7/1982 | Stournas | 252/8.55 D |

FOREIGN PATENT DOCUMENTS

| | | |
|---|---|---|
| 2095772 | 2/1972 | France . |
| 2353527 | 12/1977 | France . |
| 719445 | 12/1954 | United Kingdom . |

*Primary Examiner*—Christine M. Nucker
*Attorney, Agent, or Firm*—Alexander J. McKillop; Michael G. Gilman; James P. O'Sullivan, Sr.

[57] ABSTRACT

Novel branched alkylpolyethoxypropane sulfonate surfactants which have low interfacial tension at high salinity, and their use in enhanced oil recovery are disclosed. The surfactants have the formula $$RO(C_2H_4)_xCH_2CH_2CH_2SO_3Na$$

in which R is a branched aliphatic radical of 10 to 30 carbon atoms, and x is 2 to 6.

9 Claims, No Drawings

BRANCHED ALKYLPOLYETHOXYPROPANE SULFONATES AND THEIR USE IN ENHANCED OIL RECOVERY

CROSS-REFERENCE TO RELATED APPLICATIONS

This application is a continuation-in-part of United States Patent Applications Ser. No. 259,215 and Ser. No. 259,216, both filed Apr. 30, 1981 and both incorporated herein by reference in entirety. United States Patent Application Ser. No. 259,218, filed Apr. 30, 1981, in the name of Kirk D. Schmitt discloses an alternative method for preparing the alkylpolyethoxypropane sulfonates of this invention and is also incorporated herein by reference in its entirety.

BACKGROUND OF THE INVENTION

1. Field of the Invention

This invention is directed to branched alkylpolyethoxypropane sulfonates and a process for their use in enhancing the secondary or tertiary recovery of oil from subterranean oil deposits or reservoirs, particularly from high salinity reservoirs. In particular, branched alkylpolyethoxypropane sulfonates are suitable as single component surfactants in continuous chemical flooding techniques. They are effective over a broad range of salinity and at extremely high dilution.

II. Discussion of the Prior Art

In the recovery of oil from oil bearing deposits it is generally possible to recover only a portion of the original oil by so called "primary methods" which utilize only the natural forces present in the reservoir or deposit. Thus a variety of supplemental techniques have been employed in order to increase the recovery of oil from these subterranean reservoirs. The most widely used supplemental recovery technique is water flooding which involves injection of water into an oil bearing reservoir. However, there are problems associated with the water flooding technique and water soluble surfactants have generally been required to be used for this process to be completely successful. Thus the LTWF (Low Tension Water Flood) method using surfactants which function in low salinity (less than 3 percent) is well known. However, it has been found that preflushing the reservoirs with fresh or low salinity water to reduce the salinity so that the low salinity surfactants of the prior art may be used is not always effective, or, the preflushing is effective only for a short duration and the salinity of the fresh water increases over a period of time since it is in contact with reservoir rocks and clays. Either event renders the low salinity surfactants useless and therefore it is of vital importance to have a surfactant which functions at the salinity of the connant water to negate the necessity of preflushing.

Essentially two different concepts have developed for using surfactants to enhance oil recovery. In the first, a solution containing a low concentration of surfactants is injected into the reservoir. The surfactant is dissolved in either water or oil and is in equilibrium with aggregates of the surfactant known as micelles. Large pore volumes (about 15–60% or more) of the solution are injected into the reservoir to reduce interfacial tension between oil and water and thereby increase oil recovery. Specific relationships exist between interfacial tensions of the oil against the flooding media and the percentage recovery obtained by flooding, i.e., the efficiency of flooding increases as the interfacial tension decreases. Oil may be banked with the surfactant solution process but residual oil saturation at a given position in the reservoir will only approach zero after passage of large volumes of surfactant solution.

In the second process, a relatively small pore volume (about 3–20%) of a higher concentration surfactant solution is injected into the reservoir. With the higher surfactant concentration, the micelles become a surfactant-stabilized dispersion of either water and hydrocarbon or hydrocarbon and water. The high surfactant concentrations allow the amount of dispersed phase in the microemulsion to be high in comparison to the dispersed phase of the micelles in the low concentration surfactant solutions.

The injected solution (slug) is formulated with three or more components. The basic components (hydrocarbon, surfactant, and water) are sufficient to form the micellar solutions. A cosurfactant fourth component (usually alcohol) can be added. Electrolytes, normally inorganic salts form a fifth component that may be used in preparing the micellar solutions of microemulsions. The high concentration surfactant solutions displace both oil and water and readily displace all the oil contacted in the reservoir. As the high concentration slug moves in the reservoir, it is diluted by formation flood and the process reverts to a low concentration flood; Enhanced Oil Recovery, Van Poolen & Associates, 1980, Tulsa, Okla.

Work is still in progress in the laboratory and in the field to select the optimum method of injecting surfactant to improve oil recovery. The best process for a specific reservoir is the one which has the potential to provide the greatest efficiency and yield regardless of the concentration level of the surfactant. The chemical system, however, to be efficient must be tailored to the specific reservoir.

The prior art with respect to the use surfactant polymer floods to recover oil from reservoirs has disclosed that for a given amount of surfactant, a small slug process with a high surfactant concentration is more efficient than a large slug process with a low surfactant concentration. The former produces oil earlier but takes a smaller number of pore volumes to complete oil production. This is a favorable condition. However, it has become evident that fluid dispersion and mixing take place in the reservoirs and the slug intake routine cannot be maintained. Deterioration of the surfactant and the mobility control slug can lead to process failure or at least a reduction in process efficiency. For heterogeneous reservoirs where fluid dispersion and mixing takes place to a greater extent it is desirable if not vital to have a continuous flooding process with a surfactant which can move oil even at very low concentrations.

We have now discovered certain novel surfactants and their use in a continuous flooding process wherein low concentrations of the novel surfactant alone can be used to increase the oil production during secondary water flooding processes or to recover residual tertiary oil where the reservoirs already have been water flooded.

SUMMARY OF THE INVENTION

The present invention relates to novel branched alkylpolyethoxypropane sulfonate surfactants and the process for their use, particularly at low concentrations in enhanced oil recovery. The process is especially adaptable to high salinity reservoirs, i.e., reservoirs having a salinity of from about 4 to 30%.

The branched alkylpolyethoxypropane sulfonate, in amount effective for the intended purpose can be used as a single component surfactant without the addition of any other component or cosurfactant. However, it may be desirable to use mixtures of two or more of the branched surfactants described herein, or to use the surfactant in combination with a sacrificial agent such as lignin sulfonate. The preferred surfactants are alkylpolyethoxypropane sulfonates in which the alkyl group is branched, and which generally contains about 10 to 30 carbon atoms, preferably 12 to 20 carbons.

DESCRIPTION OF PREFERRED EMBODIMENTS

Alkylpolyethoxypropane sulfonates suitable for use in this invention have formula:

$$RO(C_2H_4O)_xCH_2CH_2CH_2SO_3Na$$

where R is a branched aliphatic radical, preferably alkyl of 10 to 30 carbon atoms. Preferably R contains 12 to 20 carbon atoms. x may vary from about 2 to 6 and is preferably 3.

The branching in the R group is preferably at least two carbon atoms. Multiple branches are not excluded. Particularly suitable surfactants are those in which R is $$R_1-\underset{\displaystyle R_2}{\underset{|}{CH}}- \quad \text{or} \quad R_3-\underset{\displaystyle R_2}{\underset{|}{CH}}-CH_2-$$

in which $R_1$ and contains 7 to 26 carbon atoms, preferably 8 to 12, $R_3$ contains 6 to 26 carbon atoms, preferably 8 to 12, and $R_2$ contains 2 to 10 carbon atoms, preferably 4 to 6.

In the above formula, the surfactant in which $R_3$ is $C_6$-alkyl and $R_2$ is $C_4$-alkyl is highly effective in reservoirs having salinity varying from about 15 to about 28 weight percent. When $R_3$ is $C_7$-alkyl and $R_2$ is $C_5$-alkyl the surfactant is very effective in salinities of from about 10 to 20 percent, and when $R_3$ is $C_8$-alkyl and $R_2$ is $C_6$-alkyl the surfactant is highly effective in salinities of from about 4 to 10 percent.

The branched sulfonates of this invention generally have their minimum interfacial tension at salinities of less than about 30%, typically at about 4 to 28%. Indeed, the surfactants can be tailored for use in particular salinity ranges by varying the overall chain length of the alkyl radical (defined as "R" above), the length of the branch or branches, and the position of the branching. In contrast to the branched surfactants of this invention whose optimum (minimum) interfacial tension occurs at salinities below about 30%, the corresponding straight chain alkyl surfactants of the prior art with the same total number of carbon atoms exhibit minimum interfacial tension at higher salinity and/or much higher Kraft temperatures. A consequence of this is that the branched surfactants exhibit significantly lower interfacial tension than the corresponding straight chain surfactants at salinities and temperatures of most interest in chemical waterflooding, viz. 30% or less and 70° C. or less. In general, at salinities of less than 30% the branched surfactants have interfacial tension values of a factor of 0.5 or less than the corresponding straight chain surfactant containing the same number of carbon atoms at the same surfactant concentration. Typically, as shown in the examples, the factor is much less than 0.5, rendering the branched surfactants of this invention particularly suitable for their intended use in waterflooding.

The branched alkylpolyethoxypropane sulfonates of this invention can be prepared by a method which, in itself, is known in the art and which is illustrated in several of the examples. The known method involves the reaction of an alkali metal salt of the branched alcohol (ROH) with propane sultone. This route provides a convenient laboratory synthesis and gives high yields but is not desirable on a large scale for several reasons. Foremost among them are the fact that (1) such a reaction requires multistep synthesis and purification of propane sultone (2) propane sultone is expensive to purify and its overall yield of 80-90% limits the yield in the preparation of propane sulfonates and (3) propane sultone is a known carcinogen. Therefore, processes involving the use of propane sultone must utilize expensive controls to minimize worker exposure but despite such controls its use will always engender some risk.

An alternative method of synthesis which has potential advantages on a commercial scale without the use of propane sultone can be conducted in accordance with the following reaction sequence.

$$RO(C_2H_4O)_xH+NaOH+CH_2{=}CH_2X \rightarrow RO(C_2H_4O)_xCH_2CH{=}CH_2+NaX \quad (I)$$

$$RO(C_2H_4O)_xCH_2CH{=}CH_2+NaHSO_3 \rightarrow RO(C_2H_4O)_xCH_2CH_2CH_2SO_3Na \quad (II)$$

R and x are as defined above and X is halogen or tosylate.

Where R is such that the allyl ether product or reaction (I) has a solubility in water of less than 0.5% the process can be conducted in two steps in a single reactor without isolation of intermediates in almost 100% yield by control of reaction conditions in steps (I) and (II). Step (I) can be carried out in a completly aqueous system if about 50% NaOH is used as the base and if close contact between the water insoluble allyl halide and alcohol is brought about by inclusion of a certain minimum amount of desired sulfonate final product in the reaction vessel. At the end of the reaction any excess allyl chloride is easily distilled from the reactor. If need not be dried but may be recycled directly, nor must it be separated from an organic solvent since no organic solvent is used.

The preparation of allyl ethers by the reaction of sodium or sodium methoxide with the alcohol followed by reaction with allyl chloride all in an organic solvent such as toluene or tetrahydrofuran (the Williamson ether synthesis) is well known and may be found in many standard textbooks on organic chemistry.

The reaction of $NaHSO_3$ with simple olefins, step (II), has been much studied. The literature teaches that for simple water-soluble olefins or olefins which can be made soluble by the addition of small amounts of alcohols, all that is required for high conversions to the desired products are conditions in which all reagents are dissolved in a single phase.

The present method of preparation is based substantially on the discovery that the branched alkylpolyethoxy allyl ethers do not behave this way. Conditions may be found in which all the reagents are dissolved in a single phase in alcohol and water and yet conversion will not exceed 40 or 50%. However, when a minor amount of propane sulfonate product is present in the reaction medium the conversion is rarely below 90%. Accordingly, it is advantageous to recycle part of the branched alkylpolyethoxypropane sulfonate final product of the reaction so that it is present during reation. In general, the propane sulfonate product is present in a molar ratio of 1:1 to about 1:10 based on the allyl ether.

EXAMPLE 1

Preparation and purification of two-tailed dodecyltriethoxypropane sulfonate (1)

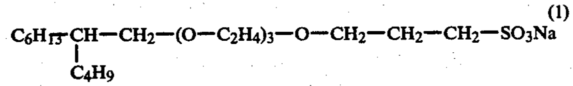

2-Butyl-1-octanol was reacted with an equivalent amount of phosphorous tribromide ($PBr_3$) at substantially 0 degrees C. 2-butyl-1-bromooctane was formed and thereafter purified by vacuum distillation. The distilled 2-butyl-1-bromooctane was ethoxylated by reacting with excess triethylene glycol. One equivalent of metallic sodium was first reacted with triethylene glycol in tetrahydrofuran as solvent. This was then followed by the addition of the bromo-compound thereto. The reaction mixture was then refluxed for 4 days. The product, triethoxylated alcohol, was purified by vacuum distillation and the purity was checked by GC. The purified triethoxylated alcohol was reacted with 0.98 equivalent of metallic sodium in toluene followed by reaction with one equivalent of distilled propane sultone dissolved in toluene. The final product, sulfonate 1, was purified by liquid chromotography . The purity of the final product was established by NMR spectroscopy.

The interfacial tension data listed below in Table 1 was obtained in the following manner:

A spinning drop Interfacial Tensiometer was used. Measurements, against a crude oil, were made after 30 minutes spinning at 10 or 14 msec., or longer, or until no more change in the drop took place. The width of the drop was then measured. The interfacial tension was calculated according to the below equation $$IFT = \frac{9.8696 \times 10^6 \times \Delta d \times \left[\frac{Dm}{66.6}\right]}{P^2}$$

where

IFT = Interfacial Tension, Dynes/cm
$\Delta d$ = difference in density between oil and brine
Dm = diameter of oil drop
P = spinning speed, msec

TABLE 1

Interfacial Tension Data
2-Tailed Dodecyltriethoxypropane Sulfonate as Single Component Surfactant

| Salinity, Percent | Concentration, Percent | IFT, dyne/cm |
|---|---|---|
| 16.6 | 2 | 0.019 |
| | 1 | 0.021 |
| | 0.5 | 0.024 |
| | 0.1 | 0.021 |
| | 0.01 | 0.016 |
| | 0.001 | 0.002 |
| 20.0 | 2 | 0.019 |
| | 1 | 0.022 |
| | 0.5 | 0.011 |
| | 0.1 | 0.008 |

TABLE 1-continued

Interfacial Tension Data
2-Tailed Dodecyltriethoxypropane Sulfonate as Single Component Surfactant

| Salinity, Percent | Concentration, Percent | IFT, dyne/cm |
|---|---|---|
| | 0.01 | 0.007 |
| | 0.001 | 0.006 |
| 26.0 | 2 | 0.005 |
| | 1 | 0.003 |
| | 0.5 | 0.017 |
| | 0.1 | 0.010 |
| | 0.01 | 0.042 |
| | 0.001 | 0.041 |

Surprisingly low tensions persisted over a span of salinity of 10 percent, and over a concentration range of three decades.

EXAMPLE 2 (COMPARATIVE)

Preparation and Purification of One-tailed Dodecyltriethoxypropane Sulfonate 2

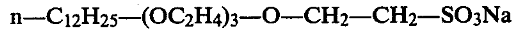

The same procedure as described in Example 1 was used except that 1-dodecanol was used in place of 2-butyl-1-octanol. The interfacial tension data for sulfonate compound (2) was obtained in the manner described in Example 1 and are listed in Table 2 below.

TABLE 2

Interfacial Tension Data
1-Tailed Dodecyltriethoxypropane Sulfonate as Single Component Surfactant

| Salinity, Percent | Concentration, Percent | IFT, dyne/cm |
|---|---|---|
| 16.6 | 2 | 0.21 |
| | 1 | 0.180 |
| | 0.5 | 0.193 |
| | 0.1 | 0.162 |
| | 0.01 | 0.140 |
| | 0.001 | 0.117 |
| 20.0 | 2 | 0.148 |
| | 1 | 0.164 |
| | 0.5 | 0.144 |
| | 0.1 | 0.150 |
| | 0.01 | 0.157 |
| | 0.001 | 0.066 |
| 22 | 0.1 | 0.178 |
| | 0.01 | 0.184 |
| | 0.001 | 0.134 |
| 26.0 | 2 | 0.085 |
| | 1 | 0.094 |
| | 0.5 | 0.066 |
| | 0.1 | 0.077 |
| | 0.01 | 0.049 |
| | 0.001 | 0.069 |

Clearly Example 2 does not produce ultra-low interfacial tension between oil and water in the specified salinity range.

EXAMPLE 3

Preparation and Purification of Two-tailed Tetradecyltriethoxypropane Sulfonate (3)

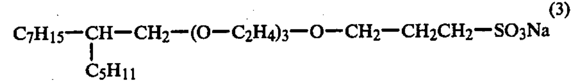

The same procedure as described in Example 1 was used except that in place of 2-butyl-1-octanol, an equivalent amount of 2-pentyl-1-nonanol was used. The interfacial tension data are listed in Table 3 (data obtained as in Example 1 above).

TABLE 3

Interfacial Tension Data
2-Tailed Tetradecyltriethoxypropane Sulfonate as a Single Component Surfactant

| Salinity, Percent | Concentration, Percent | IFT, dyne/cm |
|---|---|---|
| 10.0 | 2 | 0.019 |
| | 1 | 0.023 |
| | 0.5 | 0.027 |
| | 0.1 | 0.015 |
| | 0.01 | 0.006 |
| | 0.001 | 0.013 |
| 14.4 | 2 | 0.009 |
| | 1 | 0.008 |
| | 0.5 | 0.006 |
| | 0.1 | 0.007 |
| | 0.01 | 0.012 |
| | 0.001 | 0.055 |
| 16.6 | 2 | 0.009 |
| | 1 | 0.008 |
| | 0.5 | 0.013 |
| | 0.1 | 0.018 |
| | 0.01 | 0.037 |
| | 0.001 | 0.096 |

The $C_{14}$-alkyl produces low tension at lower salinities than the $C_{12}$ alkyl surfactant (1).

EXAMPLE 4

Preparation and Purification of Two-tailed Hexadecyltriethoxypropane Sulfonate (4)

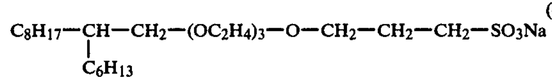

The same procedure as described in Example 1 was used except that in place of 2-butyl-1-octanol, an equivalent amount of 2-hexyl-1-decanol was used. The interfacial tension data of sulfonate (4) are listed in Table 4.

TABLE 4

Interfacial Tension Data
2-Tailed Hexadecyltriethoxypropane Sulfonate as a Single Component Surfactant

| Salinity, Percent | Concentration, Percent | IFT, dyne/cm |
|---|---|---|
| 10.0 | 1 | 0.012 |
| | 0.1 | 0.026 |
| | 0.01 | 0.040 |
| | 0.005 | 0.019 |
| 8.0 | 1 | 0.007 |
| | 0.1 | 0.007 |
| | 0.01 | 0.005 |
| 6.0 | 1 | 0.007 |
| | 0.1 | 0.005 |
| | 0.01 | 0.006 |
| | 0.005 | 0.008 |
| 4.0 | 1 | 0.019 |
| | 0.1 | 0.032 |
| | 0.01 | 0.014 |
| | 0.005 | 0.014 |
| 2.0 | 1 | 0.039 |
| | 0.1 | 0.044 |
| | 0.01 | 0.030 |
| | 0.001 | 0.033 |

EXAMPLE 5

Preparation of Propane Sulfonate of Triethoxylated 5-Dodecanol (5)

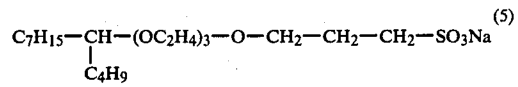

5-Dodecanol, 160 g. (0.8586 mole) was charged to a 4-neck flask fitted with a moisture trap, thermometer, nitrogen inlet tube and addition funnel. Mixed xylenes (700 ml.) were added. While the mixture was stirred magnetically, 25 ml. of xylene and traces of moisture were distilled out to the Dean-Stark trap. After 3 hrs. of reflux the trap was emptied. Then n-butyl lithium (0.8586 mole) in hexane was introduced under nitrogen. Solvent was distilled off until the pot temperature rose to 138° C. After boiling had stopped 238.5 g (0.9549 mole) of α-{2-[2-(2-Chloroethoxy)ethoxy]ethoxy}tetrahydropyran was added. The reaction mixture was refluxed under nitrogen for 114 hrs. The mixture was then cooled and filtered. Xylene was removed and the product taken up in petroleum ether. It was washed with brine and dried, then stripped of petroleum ether. the residue was dissolved in 1.8 l, of anhydrous alcohol. To the solution 37 g. of pyridine p-toluenesulfonate were added and refluxed under nitrogen for 18 hrs. An amount of 12.4 g of potassium hydroxide was added and refluxed for 2 hrs. Alcohol was stripped off. The crude product was dissolved in ether, washed with water and dried. When the ether had been removed the crude product was purified by vacuum distillation. A fraction boiling at 156° C. to 157° C. at 0.3 torr. was shown to be high purity triethoxylated 5-dodecanol by GC. The purified triethoxylated alcohol was reacted with 0.98 equivalent of metallic sodium in toluene followed by reaction with one equivalent of freshly distilled propane sultone. The final product 5 was purified by liquid chromatography. The purity of the final product was established by NMR spectroscopy. The interfacial tension data are listed in Table 5.

TABLE 5

Interfacial Tension Data
2-Tailed Secondary 5-Dodecyltriethoxypropane Sulfonate as Single Component Surfactant

| Salinity % | Concentration % | IFT, dyne/cm |
|---|---|---|
| 20 | 0.1 | 0.0078 |
| | 0.01 | 0.0033 |
| | 0.001 | 0.076 |
| 22 | 0.1 | 0.0087 |
| | 0.01 | 0.0267 |
| | 0.001 | 0.0667 |
| 24 | 0.1 | 0.0132 |
| | 0.01 | 0.0406 |
| | 0.001 | 0.108 |

EXAMPLE 6

Preparation of Propane Sulfonate of Triethoxylated 6-Tetradecanol (6)

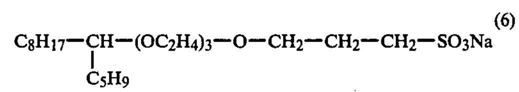

The same procedure described in Example 5 was used except that 6-tetradecanol was used in place of 5-dodecanol. The interfacial tension data of 2 are given in TABLE 6.

TABLE 6

Interfacial Tension Data
2-Tailed Secondary 6-Tetradecyltriethoxypropane Sulfonate as Single Component Surfactant

| Salinity % | Concentration % | IFT, dyne/cm |
|---|---|---|
| 6 | 0.1 | 0.0395 |
| | 0.01 | 0.0268 |
| | 0.001 | 0.0537 |
| 10 | 0.1 | 0.0029 |
| | 0.01 | 0.0027 |
| | 0.001 | 0.008 |
| 14.4 | 0.1 | 0.0054 |
| | 0.01 | 0.0238 |
| | 0.001 | 0.0417 |
| 16.6 | 0.1 | 0.0366 |
| | 0.01 | 0.0449 |
| | 0.001 | 0.091 |

It is surprising to see that low tensions persist over a span of salinity of 10% and over a concentration range of three decades.

EXAMPLE 7

155.9 grams of Berea sand (less than 325 mesh) were packed into a 6 foot glass column. The pore volume of this sand-pack column was determined to be 35 ml (by vacuum filling the dry column with brine having 16.6 percent salinity). The brine was displaced by the crude until no more brine was produced. The crude oil in the column was equivalent to the oil in a reservoir before secondary water flooding, was flooded with the 16.6 percent brine until no more oil was produced. This was, accordingly, equivalent to secondary water flooding in the field. The oil which remained in the column was equivalent to tertiary oil in th field and was determined to be 9.2 ml or 26.9 percent saturation.

Into the column containing the tertiary oil a slug of 0.2 pore volume (or 7 ml) of a 2 percent solution of sulfonate (1), prepared in Example 1, in 16.6 percent brine was injected, nothing else was added. This slug of surfactant was followed by addition of a mobility control slug consisting of 0.1 percent Xanthan gum in 1 percent NaCl solution until no more oil was produced. By this process oil started to produce when 0.87 pore volume of fluid was pumped through; 43.5 percent oil was produced after 2 pore volumes and 45 percent was produced after 3.58 pore volumes.

This clearly proves that the branched alkylpolyethoxypropane sulfonates, dodecylalkyltriethoxypropane sulfonates are suitable for use alone to enhance tertiary oil recovery without the need of a co-surfactant, even under high brine conditions.

EXAMPLE 8

An oil recovery experiment similar to that described in Example 7 was performed except that a 20 percent brine solution was used instead of a 16.6 percent solution. The results are tabulated in Table 7.

TABLE 7

Experimental Results: Oil Recovery From a Berea Sand-Pack Using 2-tailed Dodecyltriethoxypropane Sulfonate in 20 Percent Brine

| | |
|---|---|
| Weight of Sand: | 155.8 gm |
| Pore Volume: | 36.0 ml |
| Tertiary Oil: | 9.7 ml |
| Surfactant Slug: | 1.2 pv of 2 percent I in 2O percent WBB Brine |
| Mobility Control Slug: | 0.1 percent Xanthan Gum in 1 percent NaCl |
| Oil Recovery: | Started at 0.7 pv; 13.4 percent at 0.75 pv; 46.4 percent at 1.34 pv; 47.9 percent at 1.83 pv. |

The above data further show that the novel alkyltriethoxypropane sulfonates in accordance with this invention are suitable as single component surfactants in the recovery of tertiary oil under extremely high brine conditions.

EXAMPLE 9

Into a 6 ft. glass column were packed 162.8 grams of Berea sand (325 mesh). The pore volume of this sand-pack column was determined to be 39.4 ml. (by vacuum filling the dry column with 10% West Burkburnett brine). The brine was displaced by West Burkburnett crude oil until no more brine was produced. The crude oil in the column, which is equivalent to the oil in a reservoir before secondary waterflooding, was flooded with 10% West Burkburnett brine until no more oil was produced. This was equivalent to the secondary waterflooding in the field. The oil remaining in the column was the tertiary oil and was determined to be 10.0 ml of 28.6% saturation.

Into the column containing the tertiary oil was injected a slug of 1 pore volume (39.4 ml.) of a 0.3% solution of 6 (prepared Example 6) in 10% West Burkburnett brine, which also contained 1.0% lignin sulfonate and 500 ppm scleroglucan polysaccharide pusher. This slug of surfactant (6) was followed by a first mobility control slug of 0.3 pore volume of 500 ppm of scleroglucan polysaccharide in 10% brine and a second mobility control slug of 0.2 pore volume of 250 ppm of the polysaccharide in 10% brine. These slugs were followed by 10% brine until no more oil was produced. By this process 42% of the oil was produced after 1 pore volume of fluid was pumped through; 72% was produced after 1.3 pore volumes; and 82% was produced after 2.56 pore volumes.

EXAMPLE 10

Similar oil recovery experiment as described in Example 9 was performed except that 22% West Burkburnett brine was with (5) instead of 10% brine with (2). The results are tabulated in Table 8.

TABLE 8

Experimental Results: Oil Recovery from a Berea Sandpack Using Secondary 5-Dodecyltriethoxypropane Sulfonate (5)in 22% Brine

| | |
|---|---|
| Weight of Sand: | 158.1 g |
| Pore Volume: | 37.45 ml. |
| Tertiary Oil: | 9.7 ml. |
| Surfactant Slug: | 1 pv of 0.3% 1 with 1% lignin sulfonate and 5OO ppm scleroglucan polysaccharide in 22% brine |
| Mobility Control Slug: | 0.3 pv of 500 ppm scleroglucan polysaccharide, 0.2 pv of 250 ppm polysaccharide in 22% brine, followed by 22% brine only. |
| Oil Recovery | 21.6% at 1 pv; 48.5% at 1.5 pv: 78.4% at 2.57 pv. |

It is shown that (5) recovered tertiary oil under extremely high brine conditions.

EXAMPLE 11

A 6 ft. sandpack column containing 158.8 gm Berea sand was vacuum filled with 20% brine. The pore volume was determined to be 37.2 ml. The brine was displaced by crude oil until no more brine was produced. The oil in the column was then flooded with 20% brine until no more oil was produced leaving a residual oil of 9.85 ml or 26.5% residual oil saturation. The column was then flooded continuously with 0.01 wt. % of a 2-tail dodecyltriethoxypropane sulfonate (1) prepared in Example 1, in 20% brine. Oil started to produce after 0.9 pore volume; an amount of 5.2% was produced after 1.7 pv and 9% after 3.5 pv. The process is slow but incremental oil was produced.

EXAMPLE 12

The same experiment as described in Example 11 was performed except that the surfactant solution also contained 3% lignin sulfonate. 16% Oil was produced after 3.5 pore volume.

EXAMPLE 13

The same experiment as described in Example 11 was performed except that the surfactant solution was 0.1% 2-tail dodecyltriethoxypropane sulfonate (1) in 20% brine. A recovery of 12% was achieved after 4 pore volumes.

EXAMPLE 14

The same experiment was performed as described in Example 13 except that the surfactant solution also contained 3% lignin sulfonate. A recovery of 50% residual oil was achieved after 3 pore volumes and 80% after 4 pore volumes. This experiment showed that lignin sulfonate significantly improved the oil recovery.

EXAMPLE 15

The same experiment was performed as described in Example 14 except that the surfactant solution contained 1% lignin sulfonate. A recovery of 50% was achieved after 4 pore volumes and 75% after 5 pore volumes.

EXAMPLE 16

The same experiment as described in Example 11 was performed except that the 20% brine was replaced by 16.6% brine. The surfactant solution contained a 0.1 wt. % of double branched sodium dodecyltriethoxypropane sulfonate (1) and 1 wt. % lignin sulfonate as a sacrificial chemical. The column was flooded by this surfactant solution in a continuous mode, 37% tertiary oil was recovered after 2.34 pore volume and 60% after 3.74 pore volume.

EXAMPLE 17

The same experiment as described in Example 11 was performed except that 12% brine was used, the surfactant solution contained 0.1 wt. % double branched sodium tetradecyltriethoxypropane sulfonate, (3) prepared in Example 3, and 1 wt. % lignin sulfonate. The solution was injected in a continuous mode, 11.8% tertiary oil was recovered after 3.82 pore volumes, 41.2% after 5.00 and 54.1% after 6.74 pore volumes.

EXAMPLE 18

The same experiment as described in Example 11 was performed except 6% brine was used, the surfactant solution contained 0.1 wt. % of double branched sodium hexadecyltriethoxypropane sulfonate, (4) prepared in Example 4, and 1% lignin sulfonate. One pore volume of this surfactant solution was injected followed by a continuous injection of 0.15% polytran polysaccharide in 6% brine. The tertiary oil was completely recovered after 1.2 pore volume of polymer flooding.

EXAMPLE 19

This example shows that incorporation of a mobility control agent results in much earlier oil production. The sandpack with residual oil was prepared as described in Example 11. Thereafter, a surfactant solution containing 0.3 wt. % of 2-tail hexadecyltriethoxypropane sulfonate (4), 1.0 wt. % lignin sulfonate as a sacrificial chemical, and 500 ppm Polytran (a nonionic polysaccharide) in 6% brine was flooded into the sandpack column. After 1 pore volume of the surfactant solution was flooded through, tapered mobility control solutions were injected: 0.3 pore volume of 500 ppm, 0.2 pore volume of 250 ppm of Polytran in 1% NaCl followed by 1% NaCl solution. A recovery of 45% of oil was accomplished after one pore volume and 92% after 2.4 pore volume production. No pressure build up was observed.

EXAMPLE 20

Similar results to Example 19 were obtained when the mobility control slugs were in 6% brine instead of 1% NaCl.

EXAMPLE 21

Similar results to Example 19 were obtained when the 2-tail dodecyltriethoxypropane sulfonate (1) was used in 22% brine.

EXAMPLE 22

Similar results to Example 19 were obtained when the 2-tailed tetradecyltriethoxypropane sulfonate (3) was used in 12% brine.

It is clear from the Examples above that the use of the branched surfactants of this invention provides increased yields of oil from secondary and tertiary oil recovery methods. Noreover they are highly effective at very low surfactant concentrations.

What is claimed is:

1. A compound having the formula

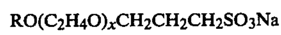

$$RO(C_2H_4O)_xCH_2CH_2CH_2SO_3Na$$

in which

R is a branched aliphatic radical containing 10 to 30 carbon atoms, in which R is the alkyl group in which $R_2$ contains 2 to 10 carbon atoms, $R_3$ contains 6 to 26 carbon atoms and x is 2 to 6.

2. The compound of claim 1 in which the branching in R is such that said compound has its minimum oil/water interfacial tension in brine of less than 30 percent, the minimum interfacial tension being a factor of 0.5 or less than that of the corresponding compound in which R is unbranched, measured at the same percent salinity.

3. A compound of claim 1 in which $R_3$ contains 8 to 12 carbon atoms and $R_2$ contains 4 to 6 carbon atoms.

4. A compound of claim 1 in which R is alkyl of the formula $$R_3-\underset{\displaystyle R_2}{\underset{|}{C}H}-CH_2-$$

in which $R_3$ contains 6 to 26 carbon atoms and $R_2$ contains 2 to 10 carbon atoms.

5. A process for recovering oil from a subterranean oil reservoir having one or more production wells and one or more injection wells in contact with said oil reservoir, comprising contacting said oil reservoir with a high salinity aqueous medium which includes as the sole surfactant, a compound having the formula $$RO(C_2H_4O)_xCH_2CH_2CH_2SO_3Na$$

in which

R is a branched aliphatic radical containing 10 to 30 carbon atoms, in which R is the alkyl group $$R_1-\underset{\displaystyle R_2}{\underset{|}{C}H}- \quad \text{or} \quad R_3-\underset{\displaystyle R_2}{\underset{|}{C}H}-CH_2-$$

in which $R_1$ contains 7 to 26 carbon atoms, $R_2$ contains 2 to 10 carbon atoms, $R_3$ contains 6 to 26 carbon atoms and x is 2 to 6, at a concentration effective to increase oil production from said production well during secondary water flooding or to recover residual tertiary oil when the oil reservoir has been previously flooded.

6. The process of claim 5 wherein said oil reservoir has a salinity of from about 4 to about 30% brine.

7. The process of claim 5 in which said aqueous medium includes a sacrificial compound in an amount effective to substantially reduce adsorption of the surfactant and thereby further increase oil production from said production well.

8. The process of claim 5 wherein the sacrificial compound is lignin sulfonate.

9. The process of claim 5 wherein the amount of lignin sulfonate is from about 0.75 to about 3 weight percent.

* * * * *

UNITED STATES PATENT AND TRADEMARK OFFICE

CERTIFICATE OF CORRECTION

PATENT NO. : 4,468,335

DATED : August 28, 1984

INVENTOR(S) : Catherine S.H. Chen & Albert L. Williams

It is certified that error appears in the above—identified patent and that said Letters Patent is hereby corrected as shown below:

Col. 12, line 58, after "alkyl group" insert this formula:

-- 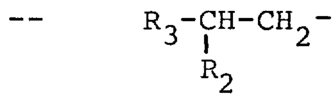 --

Signed and Sealed this

*Twelfth* Day of *February 1985*

[SEAL]

*Attest:*

DONALD J. QUIGG

*Attesting Officer* *Acting Commissioner of Patents and Trademarks*